United States Patent
Rührig

(10) Patent No.: US 8,264,222 B2
(45) Date of Patent: Sep. 11, 2012

(54) TOMOGRAPHIC MAGNETIC PARTICLE IMAGING (MPI) METHOD AND ASSOCIATED ARRANGEMENT

(75) Inventor: Manfred Rührig, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 319 days.

(21) Appl. No.: 12/071,646

(22) Filed: Feb. 25, 2008

(65) Prior Publication Data

US 2008/0218162 A1     Sep. 11, 2008

(30) Foreign Application Priority Data

Feb. 26, 2007 (DE) .......................... 10 2007 009 210

(51) Int. Cl.
*G01V 3/00* (2006.01)
(52) U.S. Cl. .......................... 324/300; 324/301; 324/302
(58) Field of Classification Search .......... 324/300–322, 324/228; 600/410, 411, 422
See application file for complete search history.

(56) References Cited

U.S. PATENT DOCUMENTS

| | | | |
|---|---|---|---|
| 6,696,838 B2* | 2/2004 | Raftery et al. | 324/321 |
| 6,958,609 B2* | 10/2005 | Raftery et al. | 324/321 |
| 7,202,667 B2* | 4/2007 | Barbic | 324/318 |
| 7,383,076 B2* | 6/2008 | Ntziachristos et al. | 600/473 |
| 7,403,008 B2* | 7/2008 | Blank et al. | 324/316 |
| 2002/0130661 A1* | 9/2002 | Raftery et al. | 324/318 |
| 2004/0058458 A1* | 3/2004 | Anker et al. | 436/526 |
| 2004/0164738 A1* | 8/2004 | Raftery et al. | 324/321 |
| 2005/0100930 A1* | 5/2005 | Wang et al. | 435/6 |
| 2006/0001423 A1* | 1/2006 | Barbic | 324/300 |
| 2006/0008924 A1* | 1/2006 | Anker et al. | 436/526 |
| 2006/0022675 A1* | 2/2006 | Blank et al. | 324/316 |
| 2006/0248945 A1* | 11/2006 | Gleich | 73/53.01 |
| 2008/0218162 A1* | 9/2008 | Ruhrig | 324/228 |
| 2008/0255006 A1* | 10/2008 | Wang et al. | 506/39 |
| 2008/0309329 A1* | 12/2008 | Kahlman et al. | 324/228 |
| 2009/0072815 A1* | 3/2009 | Kahlman et al. | 324/202 |
| 2009/0102465 A1* | 4/2009 | Jansen et al. | 324/207.21 |
| 2009/0146658 A1* | 6/2009 | McDowell et al. | 324/309 |
| 2009/0295385 A1* | 12/2009 | Brazdeikis et al. | 324/309 |
| 2010/0259251 A1* | 10/2010 | Boeve | 324/228 |
| 2010/0259259 A1* | 10/2010 | Zahn et al. | 324/309 |

(Continued)

FOREIGN PATENT DOCUMENTS

WO    WO 2006035359 A2    4/2006

(Continued)

OTHER PUBLICATIONS

Bernhard Gleich, Jürgen Weizenecker; Tomographic imaging using the nonlinear response of magnetic particles; Nature, vol. 43530, Jun. 2005—Letters, p. 1214 ff.; Magazine; 2005.

*Primary Examiner* — Melissa Koval
*Assistant Examiner* — Tiffany Fetzner
(74) *Attorney, Agent, or Firm* — Harness, Dickey & Pierce, P.L.C.

(57) ABSTRACT

According to at least one embodiment of the invention, at least two excitation fields with frequencies capable of being differently prescribed act on the object in the examination space, with the gradient field approximately vanishing in the examination space. In another embodiment, an arrangement includes a Maxwell coil pair for generating an inhomogeneous magnetic field with a prescribable magnetic field gradient, at least one device for exciting two auxiliary fields with different frequencies and a detection coil for recording the response signal.

13 Claims, 1 Drawing Sheet

U.S. PATENT DOCUMENTS

| | | | |
|---|---|---|---|
| 2011/0025323 A1* | 2/2011 | Budker et al. | 324/304 |
| 2011/0089942 A1* | 4/2011 | Goodwill et al. | 324/301 |
| 2011/0221438 A1* | 9/2011 | Goodwill et al. | 324/301 |
| 2011/0237928 A1* | 9/2011 | Rahmer et al. | 600/409 |
| 2011/0273176 A1* | 11/2011 | Weaver et al. | 324/301 |

FOREIGN PATENT DOCUMENTS

| | | |
|---|---|---|
| WO | WO 2006064405 A1 | 6/2006 |

* cited by examiner

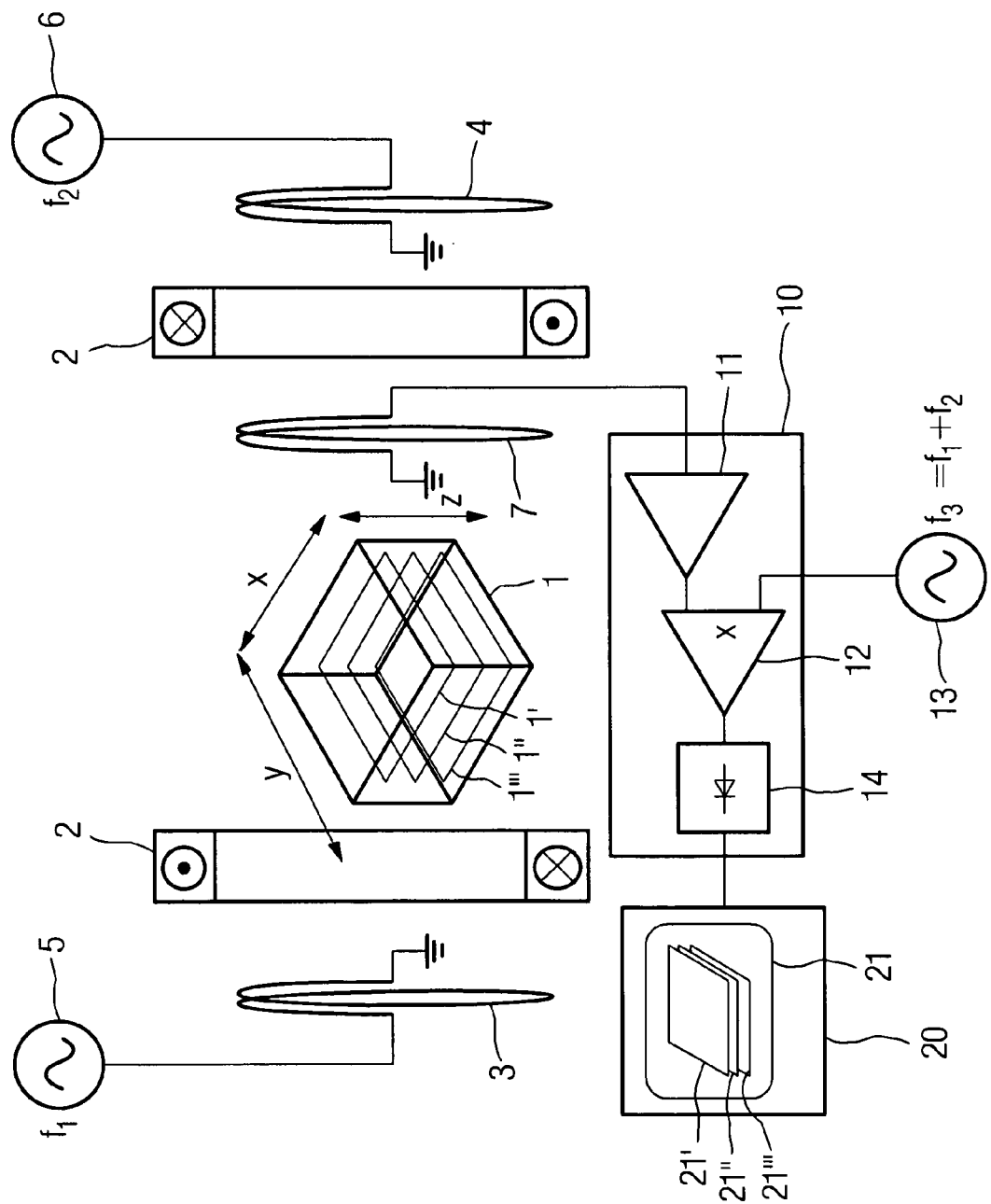

TOMOGRAPHIC MAGNETIC PARTICLE IMAGING (MPI) METHOD AND ASSOCIATED ARRANGEMENT

PRIORITY STATEMENT

The present application hereby claims priority under 35 U.S.C. §119 on German patent application number DE 10 2007 009 210.7 filed Feb. 26, 2007, the entire contents of which is hereby incorporated herein by reference.

FIELD

At least one embodiment of the invention generally relates to a tomographic imaging method for localizing magnetic particles. Alongside this, at least one embodiment of the invention also relates to an associated arrangement for carrying out the method.

BACKGROUND

The use of magnetic particles as markers in biomedical technology has long been known. In particular, following the appearance of magnetic nanoparticles it has already been proposed to use such a system for localizing magnetic markers in the form of accumulations of magnetic nanoparticles as part of analytical and/or diagnostic methods. So-called drug targeting methods, or else general tomographic imaging methods, for example, are understood here as diagnostics.

Such a tomographic imaging method in which nonlinear response signals of magnetic particles are evaluated is known from Nature, vol. 43530, June 2005-Letters, pages 1214 et seq., the entire contents of which are hereby incorporated herein by reference. Furthermore, an international patent application WO 2006/064 405 A1 is pending to this end, the entire contents of which are hereby incorporated herein by reference. The patent application describes in detail a method for determining the spatial distribution of the magnetic particles.

SUMMARY

In at least one embodiment of the invention, a method is developed to the effect that, in particular, improvements are attained in the accuracy of the analysis. There is likewise the aim, in at least one embodiment, of creating the devices suitable for a system operating using this method.

At least one embodiment of the invention is directed to a tomographic imaging method for localizing magnetic particles, in the case of which magnetic fields are applied to a system with structures to be examined, and field-free points are scanned, the induction signals generated by the particles inside the field-free space by relatively high frequency components being detected, nanoparticles are used as particles, and an alternating field is superposed on the static gradient field of the system. Use is made here of relatively high harmonics of the fundamental frequency, in particular, for evaluation purposes in order to obtain an image of the particle position, the magnetizable particles being excited with the aid of auxiliary coils of prescribed frequency, and the frequencies of odd harmonics being detected, and at least two excitation fields with frequencies capable of being differently prescribed acting in the examination space, the gradient field approximately vanishing in the examination space.

Thus, in the inventive method of at least one embodiment, in particular, use is made of two or else more alternating fields of different frequency in order to excite the magnetic particles. Consequently, a detection of a so-called intermodulation product from the fundamental frequencies used is performed, in particular, for evaluation purposes.

In accordance with at least one embodiment of the invention, a better signal-to-noise ratio is to be expected with the novel method, and this results in an improved spatial resolution. It is thereby possible for an imaging method, in particular, to achieve substantial progress in medical diagnostics.

Irrespective of the medical diagnostics, at least one embodiment of the inventive method can also be used in general laboratory analytics, preferably in materials examinations, for example nondestructive materials testing.

BRIEF DESCRIPTION OF THE DRAWINGS

Further details and advantages of embodiments of the invention emerge from the following description of the FIGURE of the example embodiment, wherein:

The sole FIGURE shows a schematic illustration of a measurement setup for examining a system with structures of interest.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the literature publication named at the beginning, a method is proposed that permits the localization of magnetic particles. This method is intended there to be used, in particular, in medical nuclear spin tomography, magnetic markers in a human body being detected, by way of example. This is performed by scanning a so-called Field Free Point (FFP) over a sample space and by having the particles produce relatively high harmonic frequency components in an induction signal inside this field-free space. The spatial resolution of this method is given in this case by the saturation field ($2 \cdot H_K$) of the particles, and the gradient of the field zero crossing $H_{Grad}$. By way of example, they should be at approximately 0.5 mm in accordance with the publication.

It is already the case that the method, long known in principle, for improving the resolution is implemented by superposing an alternating field $H^\sim$ on a static gradient field $H_{Grad}$. Relatively high harmonics of the fundamental frequency are used in this case for evaluation purposes, in order to obtain an image of the particle position. When implementing this mode of procedure in practice, a magnetizable particle, or accumulations thereof, are used to this end, for which purpose use is made of auxiliary coils with the frequency $f_0$, and the frequencies of odd harmonics are detected, for example. In detail, this is $n \cdot f_0$ with $n=3, 5, 7, 9, \ldots$ as multiplication factor of the alternating field $H^\sim$.

It is now proposed that, instead of operating with one frequency, at least two excitation fields $H^\sim_1$ and $H^\sim_2$ with the frequencies $f_1$ and $f_2$, respectively, operate in the examination space in addition to the gradient field $H_{Grad}$. It is an essential constituent of this mode of procedure that in essence an intermodulation product from the two exciter alternating fields is used for the imaging evaluation of the response signals.

The i-th order intermodulation product of two alternating fields $H^\sim_1$ and $H^\sim_2$ of frequency $f_1$, and $f_2$ is understood as the signal formed at the frequency $f_i$, the frequency $f_i$ being formed by the mathematical operation $$f_{i\,(i=n+m)} = n \cdot f_1 + m \cdot f_2 \tag{1}$$

n, m representing whole numbers.

The second order intermodulation product of the superposition of two frequencies $f_1$ and $f_2$, for example, is thereby defined as the signal that is received by the receiver coils both at the frequency $f_1+f_2$ and the frequency $f_1-f_2$. Typical frequencies $f_1$ and $f_2$ in this case are:

$f_1 = 15$ kHz,
$f_2 = 22.5$ kHz, that is to say frequencies that lie sufficiently far apart from one another.

By way of example, the evaluation electronics subsequently evaluates the frequency $f_1+f_2$, that is to say the detection frequency $f_d^1 = 37.5$ kHz, as well as possibly harmonics of lower order of $f_d^1$. Alternatively, it is also possible to use the frequency $f_1-f_2$, that is to say $f_d^2 = 7.5$ kHz for evaluation purposes. However, since the difference frequency $f_d^2$ is associated simply with exciter frequencies in this case ($2f_d^2 = f_1$, $3f_d^2 = f_2$), $f_d^2$ would be unfavorable in this case.

A suitable arrangement for such a mode of procedure is illustrated in the sole FIGURE.

In the FIGURE, 1 denotes a system with structures to be examined, for example an object to be examined or else a human body. Layer structures 1', 1", 1''', are indicated in the system 1. The system 1 is assigned a coordinate system X, Y, Z.

The system 1 to be examined is placed in an examination space of a number of coils. Present in this case on the one hand is a so-called Maxwell coil pair 2 that includes in detail of two coils geometrically offset from one another. This coil pair generates an inhomogeneous magnetic field and, specifically, a gradient field $H_{Grad}$ for the use as intended.

The coil pair 2 is respectively assigned further coils 3 and 4 that are driven with generators of different frequency, for example with the generator 4 with the frequency $f_1$, and the generator 5 with the frequency $f_2$. Assigned within the Maxwell coil pair 2 to the object 1 to be examined is a detection coil 6 with the aid of which the response signals generated by the system are detected. The signals pass from the detection coil 6 into an evaluation circuit 10 that consists in detail of an amplifier 11, a multiplication element 12 and a rectifier 13. In technical terms, the combination 11, 12 and 13 is a lock-in amplifier, that is to say a phase sensitive rectifier that amplifies all the signal components of a prescribed reference frequency and phase. If, for example, it is desired to detect all the signal components of the 1st order intermodulation product, $f_3 = f_1 + f_2$ is selected as reference frequency.

Rectification of the signals thus conditioned results in base signals that are suitable for image processing. The image processing is indicated by a display screen 21. After scanning of the object with the aid of the detection coil 7, there is yielded on the display screen 21 an image with the associated sequence of layers 21', 21", 21''' that corresponds to the sequence of layers 1', 1", 1''' of the object.

The system described above can also advantageously be used to evaluate the fundamental frequency of the intermodulation product for imaging purposes. By its nature, the fundamental frequency has a substantially higher amplitude than the harmonics, as a result of which the signal-to-noise ratio is greatly improved. This results in substantial advantages over the prior art. In the case of the literature publication discussed above, the fundamental frequency is not used at all for the evaluation, since this is identical to the frequency of the modulation field H⁻. Owing to this superposition, it seems in the case of the prior art to be possible only with great difficulty to separate the useful signal of the nanoparticles from the background signal of the excitation field at the fundamental frequency.

The evaluation device in accordance with the FIGURE and the sequence of the method steps specified in the set of claims is now used to generate a useful signal $S(f_d)$ in the magnetizable nanoparticles, specifically as intermodulation product of all the excitation frequencies. If no magnetizable material is now found at the field-free point in the object to be examined, this results in intermodulation products. The background signal at the detection frequency $f_d$ is consequently greatly reduced by comparison with the prior art.

In the case of the evaluation, specified with the aid of the FIGURE, by way of the phase sensitive lock-in technique, it is also possible not only to process the amplitude information of the marker signal $S(f_d)$, but also to detect the phase information during transversal of the field-free point by the marker position, and to utilize the information for imaging. Since the intermodulation signal constitutes, as it were, an image of the local permeability of the field-free point, it contains more information than an item purely of amplitude information that corresponds in this consideration to the real part of the permeability.

If, in addition, the phase information of the signal is also evaluated, it is possible to obtain information relating to the imaginary part of the permeability of the material at the field-free point, and this is equivalent to the hysteresis losses of the material. In a combination of the two signals it is possible in this way to obtain statements relating to complex magnetic properties, and this in turn should permit material differences to be rendered visible in the form of contrasts.

It is thereby possible by way of a difference imaging technique to further improve the resolution in the case of the specified method.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A magnetic tomographic imaging method configured for magnetic particle imaging (MPI), the method configured for localizing magnetic particles using a plurality of magnetic fields, the magnetic particles being nanoparticles used as biomedical markers, and the plurality of magnetic fields having associated different frequencies generated using two or more generators, the method comprising:

generating, by a first generator, a first frequency;

generating, by a first auxiliary coil, a first magnetic field of the plurality of magnetic fields based on the first frequency, the first generator being associated with the first auxiliary coil;

generating, by a second generator, a second frequency, the second frequency being different than the first frequency;

generating, by a second auxiliary coil, a second magnetic field of the plurality of magnetic fields based on the second frequency, the second generator being associated with the second auxiliary coil;

applying the plurality of magnetic fields to a system with structures to be examined, the structures to be examined including the magnetic particles;

scanning points where a time independent magnetic field vanishes as field-free points, the field free points being points defining a free field space in one of the plurality of magnetic fields where a magnetic particle material produces a signal including higher order harmonics as induction signals;

detecting the induction signals generated by the magnetic particles inside the field-free space;

amplifying, by a lock-in amplifier, the signal and the induction signals;

localizing the magnetic particles by superposing an alternating field on a static gradient field of the system;

obtaining an image of the position of the magnetic particles at the field-free points, using harmonics of a fundamental frequency associated with the first frequency and the second frequency, the magnetic particles being excited using the auxiliary coils of the prescribed frequencies;

detecting frequencies that differ from at least one of the first frequency and the second frequency, wherein
a gradient field associated with the first and the second magnetic fields approximately vanishes in an examination space including the system containing the structures to be examined.

2. The method as claimed in claim 1, wherein an intermodulation product of the frequencies from two alternating magnetic fields is used for imaging evaluation and defines a detection frequency.

3. The method as claimed in claim 2, wherein
the first alternating field has a frequency of 15 kHz,
the second alternating field has a frequency of 22.5kHz, as first order intermodulation product, and
at least one of the detection frequencies has a value of 37.5 kHz.

4. The method as claimed in claim 1, wherein a signal that is generated by the magnetic particles constitutes an intermodulation product of at least one of the first frequency and the second frequency.

5. The method as claimed in claim 2, wherein phase information of the two alternating magnetic fields is detected during transversal of the field free points.

6. The method as claimed in claim 1, wherein imaging is performed during the obtaining an image of the position of the particles step.

7. The method as claimed in claim 1, wherein a frequency dependence of a permeability of the magnetic particles is used as additional information when evaluating marker signals associated with at least one of the first frequency and the second frequency.

8. The method as claimed in claim 1, wherein a phase information of the induction signal is evaluated and used for at least one of analytics and diagnostics.

9. The method as claimed in claim 1, wherein materials with prescribable properties are used as the nanoparticles.

10. A magnetic tomographic imaging apparatus configured for magnetic particle imaging (MPI) by localizing magnetic particles using a plurality of magnetic fields, the magnetic particles being nanoparticles used as biomedical markers, the apparatus comprising:
a first generator configured to generate a first frequency;
a first auxiliary coil configured to generate a first magnetic field based on the first frequency, the first generator being associated with 1he first auxiliary coil;
a second generator configured to generate a second frequency, the second frequency being different than the first frequency;
a second auxiliary coil configured to generate a second magnetic field of the plurality of magnetic fields based on the second frequency, the second generator being associated with the second auxiliary coil;
a Maxwell coil pair configured to generate an inhomogeneous magnetic field having a magnetic field gradient such that the first and the second magnetic fields approximately vanish as field-free points, the field free points being points in one of the plurality of magnetic fields where a magnetic material produces a response signal including higher order harmonics as induction signals;
a detection coil configured to record the response signal associated with the magnetic field gradient; and
an evaluation device, including a lock-in amplifier configured to amplify the response signal and the induction signals, connected downstream of the detection coil.

11. The apparatus as claimed in claim 1, wherein the evaluation device is configured to drive an imaging device.

12. The method as claimed in claim 2, wherein a signal that is generated by the magnetic particles constitutes an intermodulation product of the excitation frequencies.

13. A tomographic imaging apparatus configured for magnetic particle imaging (MPI) and configured to localize magnetic particles using a plurality of magnetic fields, the plurality of magnetic fields having associated different frequencies, the apparatus including two or more means generating the different frequencies, the apparatus comprising:
a first means for generating a first frequency;
a first auxiliary means for generating a first magnetic field of the plurality of magnetic fields based on the first frequency, the first means for generating a first frequency being associated with the first auxiliary means for generating a first magnetic field;
a second means for generating a second frequency, the second frequency being different than the first frequency;
a second auxiliary means for generating a second magnetic field of the plurality of magnetic fields based on the second frequency, the second means for generating a second frequency being associated with the second auxiliary means for generating a second magnetic field;
means for applying the plurality of magnetic fields to a system with structures to be examined, the structures to be examined including the magnetic particles;
means for scanning points where a time independent magnetic field vanishes as field-free points, the field free points being points defining a free field space in one of the plurality of magnetic fields where a magnetic particle material produces a signal including higher order harmonics as induction signals;
means for detecting the induction signals generated by the magnetic particles inside the field-free space;
means for locking-in and amplifying the signal and the induction signals;
means for localizing the magnetic particles by superposing an alternating field with a static gradient field of the system;
means for obtaining an image of the position of the magnetic particles, using harmonics of a fundamental frequency associated with the first and the second frequency, the magnetic particles being excited using the auxiliary coils of the prescribed frequencies; and
means for detecting frequencies that differ from at least one of the first frequency and the second frequency, wherein
a gradient field associated with the first and the second magnetic fields approximately vanishes in an examination space including the system containing the structures to be examined.

* * * * *